United States Patent
Wietelmann et al.

(10) Patent No.: US 9,809,657 B2
(45) Date of Patent: Nov. 7, 2017

(54) LOW-VISCOSITY CONCENTRATED SOLUTIONS OF ALKALINE EARTH METAL ALKOXIDES IN APROTIC SOLVENTS AND PROCESSES FOR PREPARATION THEREOF

(71) Applicant: Rockwood Lithium GmbH, Frankfurt am Main (DE)

(72) Inventors: Ulrich Wietelmann, Friedrichsdorf (DE); Armin Stoll, Hemsbach (DE); Florian Kiefer, Goslar (DE); Ute Emmel, Frankfurt am Main (DE)

(73) Assignee: ALBEMARLE GERMANY GMBH, Frankfurt am Main (DE)

( * ) Notice: Subject to any disclaimer, the term of this patent is extended or adjusted under 35 U.S.C. 154(b) by 268 days.

(21) Appl. No.: 14/436,710

(22) PCT Filed: Oct. 25, 2013

(86) PCT No.: PCT/EP2013/072348
§ 371 (c)(1),
(2) Date: Apr. 17, 2015

(87) PCT Pub. No.: WO2014/064233
PCT Pub. Date: May 1, 2014

(65) Prior Publication Data
US 2015/0291708 A1    Oct. 15, 2015

(30) Foreign Application Priority Data
Oct. 25, 2012  (DE) .................. 10 2012 219 494

(51) Int. Cl.
| | | |
|---|---|---|
| B01J 21/00 | (2006.01) | |
| B01J 23/00 | (2006.01) | |
| B01J 25/00 | (2006.01) | |
| B01J 29/00 | (2006.01) | |
| B01J 31/00 | (2006.01) | |
| C08F 4/52 | (2006.01) | |
| C07C 41/26 | (2006.01) | |
| C07B 61/00 | (2006.01) | |

(52) U.S. Cl.
CPC ............... *C08F 4/52* (2013.01); *C07B 61/00* (2013.01); *C07C 41/26* (2013.01)

(58) Field of Classification Search
USPC ........................................ 502/100, 150, 171
See application file for complete search history.

(56) References Cited

U.S. PATENT DOCUMENTS

| | | | |
|---|---|---|---|
| 3,946,102 A * | 3/1976 | Thomas ................. | C01F 7/162 423/600 |
| 4,837,190 A | 6/1989 | Summers et al. | |
| 6,653,254 B1 | 11/2003 | Shamshoum et al. | |
| 6,734,134 B1 | 5/2004 | Gray et al. | |
| 8,148,286 B2 | 4/2012 | Dietz et al. | |
| 8,956,991 B2 * | 2/2015 | Wietelmann ............ | C07C 29/70 252/183.11 |

FOREIGN PATENT DOCUMENTS

| | | |
|---|---|---|
| EP | 0 244 917 A1 | 11/1987 |
| EP | 1 031 580 A1 | 8/2000 |
| WO | 85/02176 A1 | 5/1985 |
| WO | 2007/026016 A1 | 3/2007 |
| WO | 2010/146122 A1 | 12/2010 |

\* cited by examiner

*Primary Examiner* — James McDonough

(57) ABSTRACT

A solution of a mixed alkaline earth alkoxide compound with an aluminum compound in an aprotic solvent, and methods of making and using them.

11 Claims, No Drawings

LOW-VISCOSITY CONCENTRATED SOLUTIONS OF ALKALINE EARTH METAL ALKOXIDES IN APROTIC SOLVENTS AND PROCESSES FOR PREPARATION THEREOF

This application is a §371 of International Application No. PCT/EP2013/072348 filed Oct. 25, 2013, and claims priority from German Patent Application No. 10 2012 219 494.0 filed Oct. 25, 2012.

The invention relates to low-viscosity concentrated solutions of alkaline earth metal oxides in aprotic solvents and a method for the preparation thereof.

Magnesium alkoxides are necessary, inter alia, to prepare supported olefin polymerization catalysts of the Ziegler-Natta type. For this purpose, for example, insoluble alkoxides such as magnesium ethoxide in the form of spherical particles are used, which are converted into the active form through a reaction with titanium chloride or another compound having a titanium-halogen bond (e.g., $Cp_2TiCl_2$) (EP 1031580):

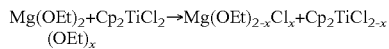

(x=0 to 2)

Another option for preparing supported Ziegler-Natta catalysts is to start with soluble magnesium alkoxides. While most magnesium alcoholates (such as magnesium salts of methanol, ethanol, propanol, isopropanol, tert-butanol, etc.) are insoluble in aprotic solvents, the magnesium compounds of primary alcohols having a branch at the 2-position prove soluble in hydrocarbons (WO 85/02176). Thus, for example, the magnesium salts of 2-methyl-1-pentanol or 2-ethyl-1-hexanol should dissolve in cyclohexane in concentrations of 1.3 mol/L. Even mixed magnesium alkoxides, meaning those with two different alkoxide radicals $Mg(OR^1)(OR^2)$, may be hydrocarbon-soluble when the corresponding alcohol $R^1OH$ is a primary alcohol branched in the 2-position and the corresponding alcohol $R^2OH$ is a secondary alcohol (WO 85/02176).

One disadvantage of hydrocarbon solutions which contain no other dissolved metal besides magnesium is their relatively high viscosities. In addition, it is not possible to prepare such solutions directly by reacting magnesium metal with the alcohol in the desired hydrocarbon without adding auxiliary agents, which have interfering effects. To enable a direct reaction at all, the magnesium metal must be activated, which can be achieved by etching with iodine. However, with this measure, the speed of reaction is still very low, even when highly-reactive magnesium powder is used. Patent document EP 0156512 thus describes the preparation of a diluted solution of magnesium-di-(2-ethylhexoxide) in dodecane, by using iodine. At a reaction temperature of 145° C., a ten-hour reaction time is necessary, and the product is obtained in the form of a viscous solution. Another option for activating magnesium is to treat the alkaline earth metal with trialkylaluminum compounds (WO 2007/026016). This method has the advantage that the product is not contaminated with iodine. However, the reaction speeds are not satisfactory, and viscous products are obtained which have a relatively high degree of contamination with protic impurities, in particular free alcohol.

To avoid the extremely long reaction times, magnesium alcoholate solutions are therefore generally prepared from commercially available dialkylmagnesium compounds ($R_2Mg$). However, this synthesis route has the disadvantage that a relatively expensive source of magnesium (namely, the $R_2Mg$ compounds, which must be prepared using haloalkanes) is used. Furthermore, a specific solvent is implicitly required, namely saturated hydrocarbons: dialkylmagnesium compounds (dibutylmagnesium, butylethylmagnesium, and butyloctylmagnesium, for example) are commercially available only in saturated hydrocarbons such as hexane or heptane. In addition, during alcoholysis according to:

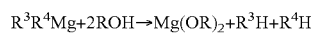

saturated hydrocarbons ($R^3H$ and $R^4H$, e.g., butane or octane), are unavoidably produced. Therefore, direct preparation of magnesium alcoholates in pure aromatic solvents such as toluene or ethylbenzene is not possible via the route of commercially available dialkylmagnesium compounds.

Another synthesis variant for preparing soluble alkaline earth alcoholates lies in the transalcoholization of insoluble alkaline earth alcoholates prepared from highly volatile alcohols (for example, ethanol) with a higher-boiling alcohol, such as:

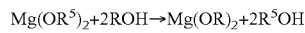

One disadvantage is the relatively high, cost-intensive level of effort required for this method: the alcoholate $Mg(OR^5)_2$ must first be prepared from the volatile alcohol $R^5OH$ and magnesium metal, isolated, then reacted with a less volatile alcohol, for example 2-ethylhexanol, and the volatile alcohol $R^5OH$ must then be removed, for example by distillation.

The relatively high viscosity of magnesium alkoxide solutions is caused by association phenomena. It is known that the viscosity can be reduced by adding alkylaluminum compounds. The preferred ratio of alkylaluminum compound to magnesium alcoholate is between 0.001:1 and 1:1, more preferably 0.01 to 0.1:1, and very especially preferably 0.03 to 0.05:1 (U.S. Pat. No. 6,734,134).

Finally, patent document WO2010/146122 discloses the preparation of mixed alkaline earth metal compounds $M(OCH_2R^6)_{2-x}(OR^7)_x$ in a mixture with an aluminum compound $Al(OCH_2R^6)_{3-y}(OR^7)_y$ in aprotic solvents starting from an alkaline earth metal and two different alcohols, wherein:

M is an alkaline earth metal selected from Mg, Ca, Ba, and Sr;

$OCH_2R^6$ is an alkoxide radical composed of at least 3 and a maximum of 40 C atoms having a branch in the 2-position, relative to the O function; i.e., $R^6$=—$CHR^8R^9$ where $R^8$, $R^9$ independently stand for alkyl radicals $C_1$-$C_{18}$;

$R^7$ is an alkyl radical containing 2-15 C atoms which is either linear or has a branch at the 3- or higher position (relative to the O function); and the sum of x and y is a number between 0.01 and 0.8, preferably between 0.02 and 0.3, and especially preferably between 0.03 and 0.2.

The product solutions prepared by this method have relatively high concentrations of alkaline earth alkoxide compounds (i.e., cMg>0.5 mol/kg), and yet the viscosities, at typically ≥1,000 cP, remain unsatisfactorily high (see also the comparative example in the present document).

A simple method is sought which, starting with an inexpensive source of magnesium and with a high space-time yield, results in less viscous, concentrated (i.e., ≥0.5, preferably ≥1.0 mol/kg) solutions of a magnesium alcoholate in aprotic solvents, preferably aliphatic or aromatic hydrocarbons. A further aim is for the desired products to have the lowest possible content of interfering impurities such as iodine, and protic materials such as alcohols and water, so that the products are suitable for preparing Ziegler-Natta catalysts.

The objective is achieved by providing mixed alkaline earth alkoxide compounds $M(OCH_2R^6)_{2-a-b}(OR^7)_a[O(CHR^8)_nOR^9]_b$ in a mixture with an aluminum compound $Al(OCH_2R^6)_{3-c-d}(OR^7)_c[O(CHR^8)_nOR^9]_d$ in aprotic solvents, wherein M is an alkaline earth metal selected from Mg, Ca, Ba, and Sr;

$OCH_2R^6$ is an alkoxide radical composed of at least 3 and a maximum of 40 C atoms having a branch in the 2-position, relative to the O function; i.e., $R^6$=—$CHR^{10}R^{11}$ where $R^{10}$, $R^{11}$ independently stand for alkyl radicals $C_1$-$C_{18}$;

$R^7$ is an alkyl radical containing 2-15 C atoms which is either linear or has a branch at the 3- or higher position (relative to the O function);

$R^8$ is an alkyl radical containing 1-6 C atoms which is either linear or has a branch at the 3- or higher position (relative to the O function);

$R^9$ is an alkyl radical containing 2-15 C atoms which is either linear or has a branch;

n=an integer between 1 and 4; and a+b≤2, c+d≤3, a and c can take any value from 0.01 to 0.8, and b and d can take any value from 0.1 to 1.99.

The aprotic solvent is, or contains, on the one hand, one or more aliphatic compounds containing 5 to 20 C atoms, whereby cyclic as well as open-chain compounds are possible. The following are preferred: cyclohexane, methylcyclohexane, hexane, heptane, octane, nonane, decane, dodecane, or decalin, as well as commercially available boiling cuts (benzene fractions).

On the other hand, the aprotic solvent can also contain or be composed of aromatics. The following are preferred: benzene, toluene, ethylbenzene, xylenes, and cumene.

In another embodiment of the invention, the alkaline earth alkoxide solution according to the invention can also contain polar aprotic solvents such as ether or tertiary amines.

The alcohol ($HOCH_2R^6$) which is branched in the 2-position is especially preferably selected from the group composed of isobutanol, 2-methyl-1-pentanol, 2-ethyl-1-butanol, 2-ethyl-1-pentanol, 2-ethyl-4-methyl-1-pentanol, 2-propyl-1-heptanol, 2-methyl-1-hexanol, 2-ethylhexanol, and 2-ethyl-5-methyl-1-octanol, or any given mixture of at least two of the listed alcohols. The primary alcohol ($HOR^7$) is preferably selected from the group composed of ethanol, propanol, butanol, pentanol, hexanol, octanol, decanol, dodecanol, 3-methylbutan-1-ol, or any given mixture of at least two of the listed alcohols. The alcohol $HO(CHR^8)_nOR^9$ containing an alkoxy function is preferably a $C_{2-4}$ glycol monoether, such as 2-ethoxyethanol, 3-ethoxy-1-propanol, 3-ethoxy-1-butanol, 2-(2-ethylhexoxy) ethanol, 2-butoxyethanol, 2-hexyloxyethanol, and 1,3-propylene glycol monobutyl ether or any given mixture of at least two of the listed alcohols.

The products according to the invention are generally prepared as follows: commercially available alkaline earth metal, preferably magnesium metal, which is preferably in the form of a powder, granules, or shavings, is placed in an anhydrous aprotic solvent, preferably aromatic or aliphatic hydrocarbons, in an agitator vessel which is rendered inert, i.e., dried and provided with a protective gas (nitrogen or argon). An alkylaluminum compound (for example, a trialkylaluminum such as triethylaluminum or tributylaluminum, an alkylaluminum hydride such as dibutylaluminum hydride, an alkylaluminum halide such as dibutylaluminum chloride, or an alkoxyaluminum compound such as diethylaluminum ethoxide) is added, and stirring is performed for five minutes to two hours at 20 to 180° C., preferably 40 to 120° C. The optimal quantity of alkylaluminum compound depends on the quality of the alkaline earth metal, in particular the quality of the magnesium, and the quantity of alcohols added in the subsequent step. The molar ratio of alkylaluminum compound to the alcohols is generally between 0.0001 and 0.1 to 1, preferably between 0.005 and 0.04 to 1.

An alcohol $HO(CHR^8)_nOR^9$ containing an alkoxy function, a branched alcohol $HOCH_2R^6$, and a primary alcohol which is unbranched or which has a branch at the 3- or higher position and contains 2-15 C atoms ($HOR^7$) are then added. The addition may be carried out either in succession in any desired sequence, or in a mixture. The primary alcohol $R^7OH$ is preferably added first, then the other two alcohols. The addition may be carried out at temperatures between 0 and 180° C., preferably between 40 and 140° C. The addition is very especially preferably carried out at the boiling point of the solvent used; thus, in the case of toluene, for example, at approximately 110° C. The reaction time depends on the reactivity of the alkaline earth metal used, in particular the magnesium, and on the acidity of the alcohol used, the stoichiometric ratio of alkaline earth metal, in particular magnesium, to the alcohols, and the reaction temperature, as well as the requirements for the end product, in particular the allowable or desired residual content of free alcohol. When the alkaline earth metal, in particular the magnesium, is used in excess (preferably in 1 to 300% excess, particularly 10 to 100% excess), a reaction time of one to six hours is sufficient when the reflux procedure is used. In contrast, products having a desired, higher residual alcohol content are prepared with excess alcohol, e.g., 5 to 20 mol %.

After the reaction is completed, which is identifiable by the cessation of the hydrogen flow, then any excess alkaline earth metal, in particular magnesium metal, which may be present is removed from the desired product solution. This can be carried out by decanting, filtration, or centrifugation.

The products prepared using the method according to the invention are of surprisingly low viscosity despite a high alkaline earth metal concentration of ≥0.5 mol/kg, preferably ≥1.0 mol/kg, and have a low content of protic impurities. The alkaline earth metal concentrations are preferably in the range of approximately 0.4 to 1.6 mmol/g, especially preferably between 0.7 and 1.4 mmol/g. The viscosities, measured at room temperature, are generally less than 300 cP, preferably less than 200 cP, especially preferably less than 100 cP. The content of protic impurities relative to the dissolved alkaline earth metal element is generally between 0.1 and 40 mol %, preferably between 1 and 30 mol %.

The content of dissolved aluminum relative to dissolved alkaline earth metal is in the range between 0.2 and 20 mol %, preferably between 1 and 8 mol %. The proportion of primary alcohol $HOR^7$, which is unbranched or which has a branch at the 3- or higher position and contains 2-15 C atoms, to the total alcohol content is between 0.5 and 40 mol %, preferably between 1 and 20 mol %, especially preferably between 1.5 and 10 mol %. The proportion of the alcohol $HO(CHR^8)_nOR^9$ containing an alkoxy function to the total alcohol content is between 5 and 99.5 mol %, preferably 10 to 99 mol %. Preferably, the production solution according to the invention contains 0.1 to 80 mol %, especially preferably 1 to 40 mol % free alcohol, relative to the alkaline earth metal present in the solution.

The products according to the invention are used for the preparation of polymerization catalysts, and in particular heterogenized polyolefin catalysts of the Ziegler-Natta type. The products according to the invention may furthermore be used in organic synthesis, in particular as bases.

EXAMPLES

All reactions were carried out in dry glass equipment rendered inert with argon. Commercially available magnesium shavings were used. The concentrations of Mg and Al were measured by inductively coupled plasma (ICP). The content of protic impurities was determined gasometrically by reaction with an approximately 1% $LiAlH_4$ solution in THF under ice cooling.

The gas quantities measured in the synthesis typically exceed the anticipated value, because the reaction hydrogen is solvent vapor-saturated, and because gaseous hydrocarbons are released from the trialkyl aluminum compound that is used (e.g., ethane from triethylaluminum).

Example 1: Preparation of Magnesium Bis(2-Butoxyethanolate) in Mixed Toluene/Heptane with the Addition of 3.5 Mol % Ethanol (Relative to the Total Alcohol Content)

13.5 g of magnesium shavings, 216 g of toluene, and 90 g of heptane were placed in a 0.5-L double-jacketed glass reactor equipped with a reflux condenser and a dropping funnel. 7.6 g of a 25% solution of triethylaluminum in toluene was then injected, and the mixture was heated to the boiling point. 2.3 g of ethanol and 163 g of 2-butoxyethanol were added dropwise over a period of 120 minutes. 15.1 L of gas was evolved (107% of theoretical yield). After the dosing, the reactor contents were refluxed for an additional 90 minutes, resulting in further evolution of 0.3 L of gas.

After cooling to approximately 80° C., the light gray suspension was siphoned off and filtered. 425 g of a non-viscous liquid was obtained which had a magnesium content of 1.26 mmol/g (corresponding to a conversion of 102% of theoretical yield). The product solution also contained 0.035 mmol/g of aluminum and had a protic impurity content of 0.23 mmol/g.

Yield: 96% of theoretical
Viscosity (Brookfield): 10 cP

Comparative Example 1: Preparation of Magnesium Bis (2-Butoxyethanolate) in Mixed Toluene/Heptane without Addition of a Primary Alcohol which is Unbranched or which has a Branch at the 3- or Higher Position and Contains 2-15 C Atoms $HOR^7$ 14.7 g of magnesium shavings, 215 g of toluene, and 90 g of heptane were placed in a 0.5-L double-jacketed glass reactor equipped with a reflux condenser and a dropping funnel. 7.6 g of a 25% solution of triethylaluminum in toluene was then injected, and the mixture was heated to the boiling point. At internal temperatures of around 104° C., 16.3 g of 2-butoxyethanol (ethylene glycol monobutyl ether) was added dropwise over a period of 90 minutes. 3.4 L of gas (24% of theoretical yield) was evolved, and the solution became increasingly viscous and dark (almost black). After the dosing, the reactor contents were refluxed for an additional four hours, resulting in further evolution of 0.6 L of gas.

After cooling to approximately 80° C., the dark gray suspension was siphoned off and filtered. 411 g of a viscous fluid having a magnesium content of 0.27 mmol/g (corresponding to a conversion of 22% of theoretical) was obtained. The product solution also contained 0.034 mmol/g of aluminum and had a protic impurity content of 2.30 mmol/g.

Yield: 18% of theoretical

Example 2: Preparation of Magnesium Bis(2-2-Ethylhexoxy)Ethanolate) in Toluene with the Addition of 1.5 Mol % Ethanol (Relative to the Total Alcohol Use)

14.7 g of magnesium shavings and 304 g of toluene were placed in a 0.5-L double-jacketed glass reactor equipped with a reflux condenser and a dropping funnel. 7.6 g of a 25% solution of triethylaluminum in toluene was then injected, and the mixture was heated to the boiling point. 0.97 g of ethanol and 236 g of 2-2(-ethylhexoxy)ethanol were added dropwise over a period of 120 minutes. 12.5 L of gas was evolved (86% of theoretical yield). After the dosing, the reactor contents were refluxed for an additional four hours, resulting in further evolution of 2.4 L of gas.

After cooling to approximately 80° C., the light gray suspension was filtered. 539 g of an almost clear liquid was obtained which had a magnesium content of 1.11 mmol/g (corresponding to a conversion of 103% of theoretical yield). The product solution also contained 0.032 mmol/g of aluminum and had a protic impurity content of 0.030 mmol/g.

Yield: 99% of theoretical
Viscosity (Brookfield): 10 cP

Comparative Example 2: Attempted Preparation of Magnesium Bis(2-(2-Ethylhexoxy)Ethanolate) in Toluene without Addition of a Primary Alcohol which is Unbranched or which has a Branch at the 3- or Higher Position and Contains 2-15 C Atoms $HOR^7$ 14.7 g of magnesium shavings and 305 g of toluene were placed in a 0.5-L double-jacketed glass reactor equipped with a reflux condenser and a dropping funnel. 7.6 g of a 25% solution of triethylaluminum in toluene was then injected, and the mixture was heated to the boiling point. 240 g of 2-2(-ethylhexoxy)ethanol was added dropwise over a period of 120 minutes. 1.2 L of gas was evolved (8% of theoretical yield). After the dosing, the reactor contents were refluxed for an additional four hours, resulting in no further evolution of any gas.

After cooling to approximately 80° C., the light gray suspension was filtered. 545 g of an almost clear liquid was obtained which had a magnesium content of <0.01 mmol/g (corresponding to a conversion of 0% of theoretical yield). The product solution also contained 0.032 mmol/g of aluminum and had a protic impurity content of 2.50 mmol/g.

Yield: 0% of theoretical

Comparative Example 3: Preparation of Magnesium Bis(2-Ethylhexanolate) in Toluene/Heptane with the Addition of 4 Mol % Ethanol in the Absence of an Alcohol Containing an Alkoxy Function $HO(CHR^8)_nOR^9$ 18.9 g of magnesium shavings, 443 g of toluene, and 40 g of heptane were placed in a 0.5-L double-jacketed glass reactor equipped with a reflux condenser and a dropping funnel. 9.6 g of a 25% solution of triethylaluminum in toluene was then injected, and the mixture was heated to the boiling point. 3.11 g of ethanol and 215 g of 2-ethylhexanole were added dropwise over a period of two hours. 14.7 L of gas was evolved (79% of theoretical yield). After the dosing, the reactor contents were refluxed for an additional 270 minutes, resulting in further evolution of 2.9 L of gas without foaming (in total, 17.6 L, or 95% of theoretical yield).

After cooling to approximately 80° C., the reaction mixture was siphoned off and filtered. 615 g of a light gray, clear liquid was obtained which had a magnesium content of 1.24 mmol/g (corresponding to a conversion of 103% of theoretical yield). The product solution also contained 0.033 mmol/g of aluminum and had a protic impurity content of 0.25 mmol/g.
Yield: 98% of theoretical
Viscosity (Brookfield): 3,700 cP Example 3: Preparation of Mixed Magnesium Bis(2-Ethylhexanolate)/Magnesium Bis(2-Butoxyethanolate) Solution in Toluene/Heptane with the Addition of 4 Mol % Ethanol (Relative to the Total Alcohol Use)

18.4 g of magnesium shavings, 443 g of toluene, and 40 g of heptane were placed in a 0.5-L double-jacketed glass reactor equipped with a reflux condenser and a dropping funnel. 9.6 g of a 25% solution of triethylaluminum in toluene was then injected, and the mixture was heated to the boiling point. 3.0 g of ethanol and a mixture of 108 g of 2-ethylhexanol and 97.5 g of 2-butoxyethanol were added dropwise over a period of two hours. 17.2 L of gas was evolved (93% of theoretical yield). After the dosing, the reactor contents were refluxed for an additional 120 minutes, resulting in further evolution of 1.8 L of gas (in total, 19.0 L, or 103% of theoretical yield).

After cooling to approximately 80° C., the reaction mixture was siphoned off and filtered. 602 g of a light gray, clear liquid was obtained which had a magnesium content of 1.26 mmol/g (corresponding to a conversion of 104% of theoretical yield). The product solution also contained 0.035 mmol/g of aluminum and had a protic impurity content of 0.23 mmol/g.
Yield: 98% of theoretical
Viscosity (Brookfield): 80 cP Comparative examples 1 and 2 were carried out according to the technical teaching of WO 2007/026016 A1; i.e., the magnesium was activated with trialkylaluminum solutions, and the reactions with the branched alcohol $HO(CHR^8)_nOR^9$ were carried out at the boiling point.

When 2-butoxyethanol was used in toluene/heptane in the absence of a primary alcohol $HOR^7$ which is unbranched or which has a branch at the 3- or higher position and contains 2-15 C atoms for a six-hour reaction time, a conversion of approximately only 18% of the theoretical yield of the desired magnesium alcoholate was obtained (comparative example 1). A strong increase in viscosity was observed. The method product also had an extremely high content of protic impurities: 2.30 mmol/g, corresponding to 370 mol % relative to dissolved magnesium. In the presence of 3.5 mol % ethanol, over a shortened reaction time of 3.5 hours, the target product was reached with 96% yield (example 1). Consequently, the content of protic impurities was very markedly decreased to only 18%. The product viscosity was extremely low (10 cP) despite the very high product concentrations.

Example 2 and comparative example show the results upon usage of a long-chain alkoxy-substituted alcohol, the 2-(2-ethylhexoxy)ethanol. In this case, it was impossible to initiate any reaction at all without the use of a primary alcohol which is unbranched or which has a branch at the 3- or higher position and contains 2-15 C atoms $HOR^7$, whereas a highly concentrated, low-viscosity solution of magnesium bis(2-(2-ethylhexoxy)ethanolate) was obtained at 99% yield when 1.5 mol % ethanol was used.

Comparative example 3 was worked in accordance with the teachings of WO2010/146122, without the use of an alcohol containing an alkoxy function $HO(CHR^8)_nOR^9$, and a highly concentrated solution of magnesium bis(2-ethylhexanolate) in toluene/heptane was prepared. The yield and the content of protic impurities were indeed in the desired ranges, but the viscosity was extremely high, at 3,700 cP.

In the last example 3, a mixture of three different alcohols was used. In this case, equal molar amounts of 2-ethylhexanol and the alcohol containing an alkoxy function, 2-butoxyethanol, were used. When 4 mol % ethanol was used, a solution containing the desired mixture of magnesium bis (2-ethylhexanolate) and magnesium bis(2-butoxyethanolate) was obtained at a very favorable yield. The viscosity was comparatively very low, at 80 cP.

The invention claimed is:

1. A solution comprising a mixed alkaline earth alkoxide compound of formula $M(OCH_2R^6)_{2-a-b}(OR^7)_a[(CHR^8)_nOR^9]_b$ in a mixture with an aluminum compound of formula $Al(OCH_2R^6)_{3-c-d}(OR^7)_c[O(CHR^8)—OR^9]_d$ in an aprotic solvent, wherein M is an alkaline earth metal selected from Mg, Ca, Ba, and Sr;

$OCH_2R^6$ is an alkoxide radical composed of at least 3 and a maximum of 40 C atoms having a branch in the 2-position, relative to O;

$R^7$ is an alkyl radical containing 2-15 C atoms which is either linear or has a branch at the 3- or higher position relative to O;

$O(CHR^8)_nOR^9$ is an alkoxide radical in which
  $R^8$ is an alkyl radical containing 1-6 C atoms which is either linear or has a branch at the 3- or higher position relative to O;
  $R^9$ is an alkyl radical containing 2-15 C atoms which is either linear or has a branch;
  n is an integer between 1 and 4;

$a+b \leq 2$;

$c+d \leq 3$;

a and c are from 0.01 to 0.8; and b and d each range from 0.1 to 1.99; and wherein the solution has a content of aluminum relative to the alkaline earth metal in the range between 0.2 and about 20 mol %.

2. The solution according to claim 1, characterized in that the alkaline earth metal has a concentration in the range of 0.4 to 1.6 mmol/g.

3. The solution according to claim 1, characterized in that the solution has a viscosity of ≤300 cP at room temperature.

4. The solution according to claim 1, characterized in that the solution has a content of protic impurities relative to the alkaline earth metal between 0.1 and 40 mol %.

5. The solution according to claim 1, wherein $O(CHR^8)_nOR^9$ is derived from a $C_2$-$C_4$ glycol monoether.

6. The solution according to claim 1, wherein $O(CHR^8)_nOR^9$ is derived from an alcohol selected from the group consisting of 2 ethoxyethanol, 3-ethoxy-1-propanol, 3-ethoxy-1-butanol, 2-(2-ethylhexoxy) ethanol, 2-butoxyethanol, 2-hexyloxyethanol and 1,3-propylene glycol monobutyl ether.

7. The solution according to claim 1, characterized by containing 0.1 to 80 mol % free alcohol relative to the alkaline earth metal.

8. A method comprising preparing Ziegler-Natta polymerization catalysts with a solution of claim 1.

9. A method comprising performing an organic synthesis, wherein a solution of claim 1 is used in the organic synthesis.

10. The solution according to claim 1, characterized in that in the alkoxide radical $OCH_2R^6$, $R^6$ is $-CHR^{10}R^{11}$ where $R^{10}$ and $R^{11}$ independently stand for alkyl radicals having 1 to 18 carbon atoms.

11. The solution according to claim 1, characterized in that in the aprotic solvent is an aliphatic hydrocarbon or an aromatic hydrocarbon selected from the group consisting of cyclohexane, methylcyclohexane, hexane, heptane, octane, nonane, decane, dodecane, decalin, and commercially available benzene fractions, benzene, toluene, ethylbenzene, xylenes, and cumene.

* * * * *

UNITED STATES PATENT AND TRADEMARK OFFICE
CERTIFICATE OF CORRECTION

PATENT NO.       : 9,809,657 B2
APPLICATION NO.  : 14/436710
DATED            : November 7, 2017
INVENTOR(S)      : Ulrich Wietelmann et al.

It is certified that error appears in the above-identified patent and that said Letters Patent is hereby corrected as shown below:

In the Claims

Column 8, Claim 1, Lines 26-27, read "formula $M(OCH_2R^6)_{2-a-b}(OR^7)_a[(CHR^8)_nOR^9]_b$ in" and should read -- formula $M(OCH_2R^6)_{2-a-b}(OR^7)_a[O(CHR^8)_nOR^9]_b$ in --

Signed and Sealed this
Twenty-ninth Day of May, 2018

Andrei Iancu
*Director of the United States Patent and Trademark Office*